United States Patent [19]

Itoh et al.

[11] Patent Number: 4,898,931

[45] Date of Patent: Feb. 6, 1990

[54] NOVEL HUMAN INTERFERON-γ POLYPEPTIDE DERIVATIVE

[75] Inventors: Seiga Itoh, Sagamihara; Yasutoshi Takeichi; Moriyuki Sato, both of Machida, all of Japan

[73] Assignee: Kyowa Hakko Kogyo Co., Ltd., Tokyo, Japan

[21] Appl. No.: 751,205

[22] Filed: Jul. 10, 1985

[30] Foreign Application Priority Data

Jul. 11, 1984 [JP] Japan ................. 59-143950

[51] Int. Cl.$^4$ ............ C07K 13/00; C07K 15/26; A61K 45/02
[52] U.S. Cl. .................. 530/351; 424/85.5; 435/69.51
[58] Field of Search ........... 435/68, 511; 530/351; 424/85, 85.5

[56] References Cited

U.S. PATENT DOCUMENTS 4,457,867 7/1984 Ishida .................. 530/351
4,727,138 2/1988 Goeddel et al. ........... 536/27

FOREIGN PATENT DOCUMENTS 0083777 7/1983 European Pat. Off. .
0095350 11/1983 European Pat. Off. .
0103898 3/1984 European Pat. Off. .
0112976 7/1984 European Pat. Off. .
0146944 7/1985 European Pat. Off. .
WO83/04053 11/1983 World Int. Prop. O. .

OTHER PUBLICATIONS

Shepard et al, Nature, vol. 294, pp. 563–565, 1981.
K. Alton et al., "Production, Characterization and Biological Effects of Recombinant DNA Derived Human IFN-α and IFN-γ Analogs", The Biology of the Interferon System 1983, Elsevier Science Publishers B.V., pp. 119–127.
B. Rubin et al., Proc. Natl. Acad. Sci., USA, vol. 77, No. 10, pp. 5928–5932 (Oct. 1980).
P. Gray et al., Nature, vol. 295, pp. 503–508 (Feb. 11, 1982).
R. Devos et al., Nucleic Acids Research, vol. 10, No. 8 (1982).
A. Franke et al., DNA, vol. 1, No. 3, pp. 223–230 (1982).
R. King et al., J. Gen. Virol., 64, 1815–1818 (1983).
Nishi et al., DNA, vol. 2, No. 4, pp. 265–273 (1983).
Itoh et al., DNA, vol. 3, No. 2, pp. 157–165 (1984).
Gray et al., Proc. Natl. Acad. Sci. USA, vol. 80, pp. 5842–5846 (1984).

*Primary Examiner*—Blondel Hazel
*Attorney, Agent, or Firm*—Fitzpatrick, Cella, Harper & Scinto

[57] ABSTRACT

Disclosed is a novel derivative of human IFN-γ polypeptide wherein certain amino acids of human IFN-γ polypeptide are removed and certain amino acids other than said amino acids are replaced with other amino acids. The derivatives have high IFN-γ activity and are expected to be useful as drugs such as anti-viral and anti-tumor agents.

1 Claim, 4 Drawing Sheets

FIG.2

NOVEL HUMAN INTERFERON-γ POLYPEPTIDE DERIVATIVE

BACKGROUND OF THE INVENTION

Interferons (referred to as IFN hereinafter) so far known can be classified into three groups, i.e., IFN-α, IFN-β and IFN-γ. IFN-α is mainly produced from leukocytes, IFN-β from fibroblasts and IFN-γ from T-lymphocytes. These IFNs have been noted as biologically active substances having anti-virus activity, activating activities upon natural killer cells and macrophages, antitumor activity, and the like.

As for IFN-γ, there has been a report that it has a stronger cell-inhibiting activity than other IFNs based on the experiment using animal cells [B. Y. Rubin and S. L. Gupta: Proc. Natl. Acad. Sci., USA, 77, 5928–5932 (1980)]. Furthermore, cloning of an IFN-γ cDNA and determination of its base sequence were recently reported [P. W. Gray, et al.: Nature 295, 503 (1982), R. Devos, et al.: Nucleic Acids Research 10, 2487 (1982)].

The present inventors have independently cloned a cDNA coding for a novel IFN-γ wherein, as apparent from the base sequence illustrated in Table 1, the ninth amino acid of the mature IFN-γ reported by Devos, et al., Lysine (Lys) (AAA), is replaced with glutamine (Gln) (CAA). Further, the IFN-γ cDNA was incorporated into vector pKYP-10 having a tryptophan promoter (Japanese Published Unexamined Patent Application No. 110600/83) and mass production of the IFN-γ in *Escherichia coli* has been achieved.

Thereafter, the present inventors have studied the production of derivatives of IFN-γ polypeptide using the IFN-γ cDNA illustrated in Table 1 as a starting material.

It was reported that deletion of 11 amino acids from the C-terminal of IFN-α decreased specific activity to one-third [A. E. Franke, et al.: DNA 1, 223–230 (1982)], whereas addition of 18 amino acids to the N-terminal of IFN-α did not change specific activity [R. M. King, et al.: J. Gen. Virol. 64, 1815–1818 (1983)].

The present inventors have found that deletion of 5 amino acids from the N-terminal of IFN-β decreased specific activity to about 1/100 [T. Nishi, et al.: DNA 2, 265–273 (1983)] and addition of 7 amino acids to the N-terminal of IFN-β decreased specific activity to about 1/10 [S. Itoh, et al.: DNA 3, 157–165 (1984)].

The present inventors have constructed a derivative of IFN-γ wherein the third amino acid of IFN-γ illustrated in Table 1, cysteine (Cys), was replaced with tyrosine (Tyr) (referred to as 3-Tyr-IFN-γ hereinafter) and found that the specific activity was 2–4 times as strong as that of the parent IFN-γ. Further, the derivatives wherein the Cys at the position 1 was replaced with serine (Ser) (1-Ser-IFN-γ), the Cys at the position 3 was replaced with Ser (3-Ser-IFN-γ), the Cys at the positions 1 and 3 were replaced with Ser (1,3-Ser-IFN-γ) and N-terminal amino acids of IFN-γ illustrated in Table 1 were deleted were constructed. Equivalent or more interferon activity was detected for all the derivatives compared with the starting IFN-γ.

It has been known that murine mature IFN-γ consists of 136 amino acids, which number is less by 10 than that of amino acids of human IFN-γ, and is more heat-stable than human IFN-γ. Murine IFN-γ has Cys at the position 136 as well as at the positions 1 and 3 and these Cys form disulfide bonds in the molecule, which are considered to contribute to stabilization of IFN [D. Goeddel, et al.: Proc. Natl. Acad. Sci. USA 80, 5842–5846 (1984)].

The present inventors have prepared the molecular model of IFN-γ and assumed that the formation of disulfide bond in the molecule of human IFN-γ was possible by introducing Cys between the positions 135 and 138 from the N-terminal, preferably at the position 137. Several derivatives of IFN-γ wherein C-terminal amino acids were deleted and Met at the position 137 was replaced with Cys have been found to have increased heat stability and specific activity.

SUMMARY OF THE INVENTION

The present invention relates to a novel derivative of human IFN-γ polypeptide wherein certain amino acids of human IFN-γ polypeptide are removed and certain amino acids other than said amino acids are replaced with other amino acids. The novel derivatives have high IFN-γ activity and are expected to be useful as drugs such as anti-viral and anti-tumor agents.

DETAILED DESCRIPTION OF THE INVENTION

An object of the present invention is to provide a recombinant plasmid wherein a DNA coding for a novel derivative of human IFN-γ is incorporated, a microorganism containing the plasmid, a process for producing a novel derivative of human IFN-γ polypeptide using the microorganism and the derivative of human IFN-γ polypeptide per se.

Construction of the recombinant plasmid is carried out using cDNA obtained from messenger RNA coding for IFN-γ by recombinant DNA technology or chromosomal DNA coding for IFN-γ as a starting material.

In the present invention, any human IFN-γ cDNA is employable and pIFNγ-G4 is preferably used. *Escherichia coli* containing pIFNγ-G4 has been deposited with the American Type Culture Collection, USA under accession number ATCC 39123.

The DNA sequence of the IFN-γ DNA in pIFNγ-G4 was determined by the method of Maxam and Gilbert [Proc. Natl. Acad. Sci. 74, 560 (1977)] and is illustrated in Table 1.

TABLE 1

CACATTGTTCTGATCATCTGAAGATCAGCTATTAGAAGAGAAAGATCAGTTAAGTCCTTTGGACCTGATCAGCTTGA

TABLE 1-continued

```
                                                       -20
                                                       met lys tyr thr ser tyr ile leu
TACAAGAACTACTGATTTCAACTTCTTTGGCTTAATTCTCTCGGAAACG ATG AAA TAT ACA AGT TAT ATC TTG 1                              10
ala phe gln leu cys ile val leu gly ser leu gly CYS TYR CYS GLN ASP PRO TYR VAL  GLN  GLU
GCT TTT CAG CTC TGC ATC GTT TTG GGT TCT CTT GGC TGT TAC TGC CAG GAC CCA TAT GTA  CAA  GAA
                                                    1                             ↑

20                                          30
ALA GLU ASN LEU LYS LYS TYR PHE ASN ALA GLY HIS SER ASP VAL ALA ASP ASN GLY THR LEU PHE
GCA GAA AAC CTT AAG AAA TAT TTT AAT GCA GGT CAT TCA GAT GTA GCG GAT AAT GGA ACT CTT TTC 40                                          50
LEU GLY ILE LEU LYS ASN TRP LYS GLU GLU SER ASP ARG LYS ILE MET GLN SER GLN ILE VAL SER
TTA GGC ATT TTG AAG AAT TGG AAA GAG GAG AGT GAC AGA AAA ATA ATG CAG AGC CAA ATT GTC TCC 60                                          70
PHE TYR PHE LYS LEU PHE LYS ASN PHE LYS ASP ASP GLN SER ILE GLN LYS SER VAL GLU THR ILE
TTT TAC TTC AAA CTT TTT AAA AAC TTT AAA GAT GAC CAG AGC ATC CAA AAG AGT GTG GAG ACC ATC 80                                          90
LYS GLU ASP MET ASN VAL LYS PHE PHE ASN SER ASN LYS LYS LYS ARG ASP ASP PHE GLU LYS LEU
AAG GAA GAC ATG AAT GTC AAG TTT TTC AAT AGC AAC AAA AAG AAA CGA GAT GAC TTC GAA AAG CTG 100                                        110                              120
THR ASN TYR SER VAL THR ASP LEU ASN VAL GLN ARG LYS ALA ILE HIS GLU LEU ILE GLN VAL MET
ACT AAT TAT TCG GTA ACT GAC TTG AAT GTC CAA CGC AAA GCA ATA CAT GAA CTC ATC CAA GTG ATG 130                                        140
ALA GLU LEU SER PRO ALA ALA LYS THR GLY LYS ARG LYS ARG SER GLN MET LEU PHE  ARG   GLY
GCT GAA CTG TCG CCA GCA GCT AAA ACA GGG AAG CGA AAA AGG AGT CAG ATG CTG TTT  CGA   GGT
                                                                             (↑)

146
ARG ARG ALA SER GLN
CGA AGA GCA TCC CAG TAA TGGTTGTCCTGCCTGCAATATTTGAATTTTAAATCTAAATCTATTTATTAATATTTAA

CATTATTTATATGGGGAATATATTTTTAGACTCATCAATCAAATAAGTATTTATAATAGCAACTTTTGTGTAATGAAA

ATGAATATCTATTAATATATGTATTATTTATAATTCCTATATCCTGTGACTGTCTCACTTAATCCTTTGTTTTCTGACTA

ATTAGGCAAGGCTATGTGATTACAAGGCTTTATCTCAGGGGCCAACTAGGCAGCCAACCTAAGCAAGATCCCATGG

GTTGTGTGTTTATTTCACTTGATGATACAATGAACACTTATAAGTGAAGTGATACTATCCAGTTACTA CCCCCCC...
                                                                   ↑
```

Comparison of the human IFN-γ cDNA in pIFNγ-G4 and the known IFN-γ cDNA [R. Devos, et al.: Nucleic Acids Research, 10, 2487 (1982)] reveals the following. The first base of the triplet coding for the ninth amino acid from the N-terminal of the mature human IFN-γ polypeptide lysine, in the known cDNA is adenine (A) [R. Devos, et al.: Nucleic Acids Research, 10, 2487 (1982)]. On the other hand, as the corresponding base in the pIFNγ-G4 cDNA is cytosine (C), the ninth amino acid from the N-terminal of the human IFN-γ polypeptide encoded by the pIFNγ-G4 cDNA is glutamine, and not lysine. Therefore, it is apparent that pIFNγ-G4 codes for a novel human IFN-γ polypeptide.

Derivatives of IFN-γ obtained by deletion or replacement of amino acids of IFN-γ illustrated in Table 1 are also novel IFN-γ derivatives.

As the plasmid to incorporate a DNA coding for IFN-γ derivative, any plasmid can be used so long as the DNA incorporated therein can be expressed in *Escherichia coli*. Preferably, a plasmid wherein a foreign DNA can be inserted downstream from a suitable promoter such as tryptophan promoter (Prtrp), lac promoter or P_L promoter of γ phage and the length between Shine-Dalgarno sequence (referred to as SD sequence hereinafter) and initiation codon (ATG) is adjusted, for example, to 6-18 base pairs is employed. Preferred examples are pKYP10, pKYP11 and pKYP12 which were constructed by the present inventors (Japanese Published Unexamined Patent Application No. 110600/83).

Figure 1:
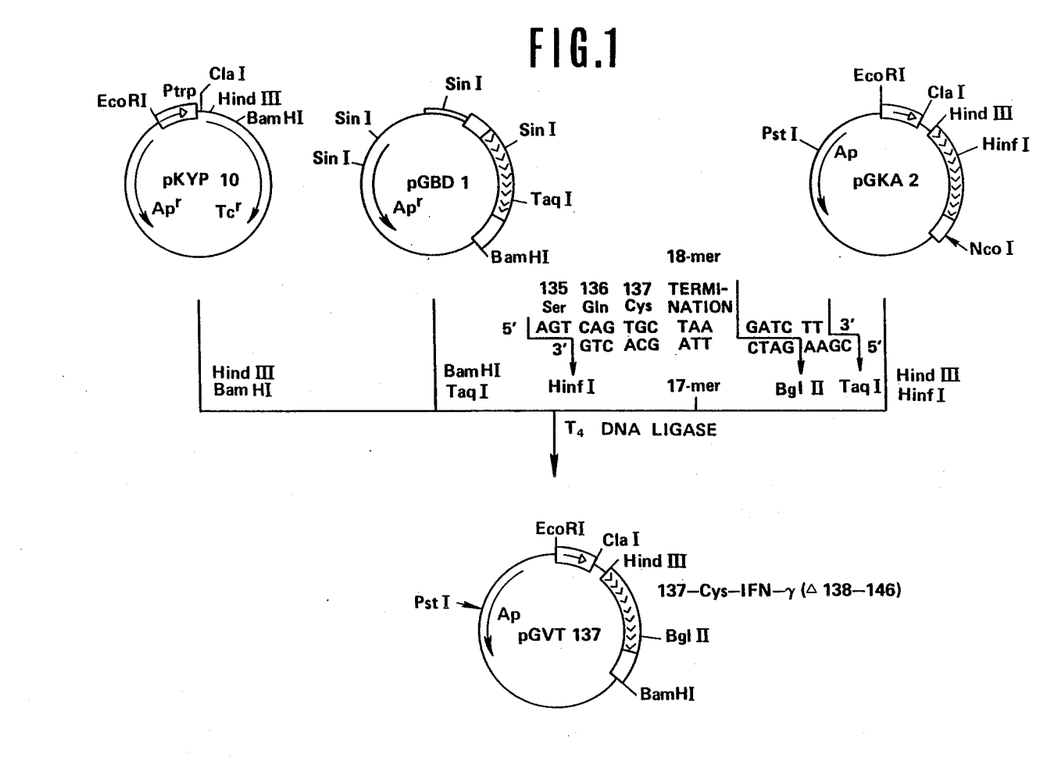
FIG. 1 is a flow sheet for the construction of plasmid pGVT137. As the sites for HinfI and TaqI, only those which are used for the construction are indicated.

As illustrated in FIG. 1, pGBD1 (Reference Example 1) is cleaved with BamHI and TaqI, and the digest is purified by polyacrylamide gel electrophoresis [A. M. Maxam, et al.: Proc. Natl. Acad. Sci. USA 74, 560 (1977)] to obtain a DNA fragment of about 310 base pairs (referred to as bp hereinafter).

Then, pGKA2 (Reference Example 2) is cleaved with HindIII and HinfI, and a DNA fragment of about 400 bp containing a large portion of the IFN-γ structural gene is obtained by polyacrylamide gel electrophoresis.

pKYP10 (Japanese Published Unexamined Patent Application No. 110600/83) is cleaved with HindIII and BamHI to obtain a DNA fragment of about 4.3 Kb containing a tryptophan promoter. Separately, in order to obtain an IFN-γ derivative wherein the amino acid at the position 137 of mature human IFN-γ polypeptide, Met, is replaced with Cys and the amino acids at the positions 138-146 are deleted, the DNA linker illustrated below is synthesized.

The purified DNA fragments and the synthetic DNA linker are ligated with T4 DNA ligase to obtain the recombinant plasmid pGVT137 illustrated in FIG. 1. The plasmid codes for the IFN-γ derivative [137-Cys-IFN-γ (Δ138-146)] which has Cys as the amino acid at the position 137 and does not have the amino acids at the positions 138-146.

Then, in order to construct the recombinant pGNC5 coding for the derivative [1-Ser-137-Cys-IFN-γ(Δ138-146)], pGVL10 (Reference Example 4) is cleaved with HindIII and TaqI and a DNA fragment of about 300 bp is obtained. Separately, pGVT137 DNA obtained in Example 1 is cleaved with BglII and TaqI, and HindIII and BglIII, respectively to obtain DNA fragments of about 130 bp and about 4.6 Kb. The DNA fragments are ligated with T4 DNA ligase to obtain the recombinant plasmid pGNC5 illustrated in FIG. 2.

The recombinant plasmid pGNB4 coding for 3-Ser-137-Cys-IFN-γ(Δ138-146) and the recombinant plasmid pGNA3 coding for 1,3-Ser-137-Cys-IFN-γ(Δ138-146) are constructed by the same method as described above except that the plasmids pGVM101 (FIG. 3) and pGVK13 (FIG. 4) are respectively used as the source of DNA coding for the N-terminal region of IFN-γ.

Reaction conditions required for the recombinant DNA technology described above are generally as follows.

Digestion of the DNA with restriction enzymes is usually carried out by reacting 0.1 to 20 μg of DNA with 0.1-100 units, preferably 1-3 units of restriction enzyme per 1 μg of DNA in a mixture of 2-200 mM, preferably 10-40 mM Tris-HCl (pH 6.0-9.5, preferably pH 7.0-8.0), 0-200 mM NaCl and 2-20 mM, preferably 5-10 mM $MgCl_2$ at 20°-70° C. (optimal temperature depends on restriction enzymes used) for 15 minutes to 24 hours. Reaction is usually stopped by heating at 55°-75° C. for 5-30 minutes, or alternatively by inactivating the restriction enzyme with a reagent such as phenol or diethylpyrocarbonate.

Purification of the DNA fragments formed by digestion with restriction enzymes is carried out by low-gelling-temperature agarose gel electrophoresis [L. Wieslander: Analytical Biochemistry 98, 305 (1979), hereinafter referred to as LGT method] or polyacrylamide gel electrophoresis.

Ligation of the DNA fragments is carried out with 0.3-10 units of T4 DNA ligase in a mixture of 2-200 mM, preferably 10-40 mM Tris-HCl (pH 6.1-9.5, preferably 7.0-8.0), 2-20 mM, preferably 5-10 mM $MgCl_2$, 0.1-10 mM, preferably 0.5-2.0 mM ATP and 1-50 mM, preferably 5-10 mM dithiothreitol at 1°-37° C., preferably 3°-20° C. for 15 minutes to 72 hours, preferably, 2-20 hours. The recombinant plasmid DNA formed by the ligation reaction is introduced into Escherichia coli by the transformation method of Cohen, et al. [S. N. Cohen, et al.: Proc. Natl, Acad. Sci. USA 69, 2110 (1972)], if necessary. Isolation of the recombinant plasmid DNA from Escherichia coli carrying the DNA is carried out by the method described in Example 1 or the method of Birnboim, et al. [H. C. Birnboim, et al.: Nucleic Acids Res. 7, 1513 (1979)]. Plasmid DNA is digested with 1-10 kinds of restriction endonucleasees and the cleavage sites are examined by agarose gel electrophoresis or polyacrylamide gel electrophoresis. Further, if necessary, the DNA sequence of the DNA is determined by the method of Maxam-Gilbert [Proc. Natl. Acad. Sci. 74, 560 (1977)].

The recombinant plasmids can be prepared under the above-described conditions.

The derivative of IFN-γ polypeptide of the present invention is produced by the following method.

That is, Escherichia coli K-12 HB101 is transformed with a plasmid such as pGVA4 and an Escherichia coli strain carrying pGVA4 is selected from the ampicillin resistant (referred to as $Ap^R$ hereinafter) colonies. The Escherichia coli strain carrying pGVA4 is cultured in a medium to produce a derivative of IFN-γ polypeptide in the medium.

As the medium, either a synthetic medium or a natural medium can be used as long as it is suitable for the growth of Escherichia coli and the production of the derivative of IFN-γ polypeptide.

As a carbon source, glucose, fructose, lactose, glycerol, mannitol, sorbitol, etc. may be used.

As a nitrogen source, $NH_4Cl$, $(NH_4)_2SO_4$, casamino acid, yeast extract, polypeptone, meat extract, Bacto-trypton, corn steep liquor, etc. may be used.

In addition, nutrients such as $K_2HPO_4$, $KH_2PO_4$, NaCl, $MgSO_4$, vitamine $B_1$ and $MgCl_2$ may be used.

Culturing is carried out at pH 5.5-8.5 and at 18°-40° C. with aeration and stirring.

After culturing for 5-90 hours, the derivative of human IFN-γ polypeptide is accumulated in cultured cells. The collected cells are treated with lysozyme, disrupted by repeated freezing and thawing and subjected to centrifugation. The thus obtained supernatant fluid is subjected to extraction according to a conventional method for extraction of polypeptide to recover the polypeptide.

Determination of the human IFN-γ activity is carried out according to the method of Armstrong [J. A. Armstrong, et al.: Appl. Microbiol. 21, 723-725 (1971)].

Certain specific embodiments of the present invention are illustrated by the following examples.

EXAMPLE 1

Construction of recombinant plasmid pGVT137 coding for 137-Cys-IFN-γ (Δ138-146)

In this step, 10 μg of pGBD1 DNA obtained in Reference Example 3 was dissolved in 50 μl (total volume) of a solution consisting of 20 mM Tris-HCL (pH 7.5), 10 mM MgCl₂, 10 mM dithiotreitol and 100 mM NaCl (referred to as "Y-100 buffer solution" hereinafter). Then, 20 units of restriction enzyme BamHI (product of Takara Shuzo Co., the restriction enzymes hereinafter are all products of Takara Shuzo Co. unless otherwise specified) was added and digestion reaction was carried out at 37° C. for 3 hours. Subsequently, 20 units of restriction enzyme TaqI was added and digestion reaction was carried out at 65° C. for 2 hours. About 0.5 μg of a DNA fragment of about 310 bp containing 3' non-translational region was obtained from the reaction solution by polyacrylamide gel electrophoresis.

Separately, 10 μg of pGKA2 DNA obtained in Reference Example 2 was dissolved in 50 μl (total volume) of a solution containing Y-100 buffer solution and 20 units each of restriction enzymes HindIII and HinfI were added to the solution. Digestion reaction was carried out at 37° C. for 3 hours. A DNA fragment of about 400 bp containing a large portion of the IFN-γ structural gene was obtained from the reaction solution by polyacrylamide gel electrophoresis. 3 μg of pKYP10 DNA prepared by the method described in Japanese Published Unexamined Patent Application No. 110600/83 was dissolved in 40 μl (total volume) of a solution containing Y-100 buffer solution and 6 units each of restriction enzymes HindIII and BamHI were added to the solution. Digestion reaction was carried out at 37° C. for 3 hours. 1.8 μg of a DNA fragment of about 4.3 Kb containing a tryptophan promoter (Ptrp) was obtained from the reaction solution by LGT method. Separately, in order to change the 137th amino acid (Met) of the mature human IFN-γ polypeptide to Cys and to furnish a terminal codon (TAA) necessary for the termination of expression immediately after the 137th Cys, the following DNA linker was synthesized.

Co.) was added and phosphorylation reaction was carried out at 37° C. for 60 minutes.

Then, 0.5 μg of the TaqI-BamHI fragment of about 310 bp derived from pGBD1, 0.5 μg of the HindIII-HinfI fragment of about 400 bp derived from pGKA2 and 1.0 μg of the HindIII-BamHI fragment of about 4.3 Kb of the expression vector pKYP10 which were obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

*Escherichia coli* HB101 was transformed using the resulting recombinant plasmid mixture to obtain an Ap^R colony. Plasmid pGVT137 illustrated in FIG. 1 was isolated from the culture broth of the colony. The structure of pGVT137 was confirmed by the digestion with EcoRI, ClaI, BglII and BamHI and agarose gel electrophoresis. It was confirmed by the method of Maxam-Gilbert [A. M. Maxam, et al.: Proc. Natl. Acad. Sci., USA, 74, 560 (1977)] that the DNA sequence around HinfI-TaqI in the plasmid pGVT137 was as follows.

The human IFN-γ polypeptide derivative encoded by pGVT137 [the derivative is named 137-Cys-IFN-γ(Δ138-146)] is clearly different from the known human IFN-γ polypeptide in that the 137th amino acid (Met) of the mature human IFN-γ is replaced with Cys and the 9 amino acids from the C-terminal 138th amino acid (Leu) to the 146th amino acid (Gln) are deleted.

*Escherichia coli* strain carrying plasmid pGVT137 has been deposited with the Fermentation Research Institute, Agency of Industrial Science and Technology (referred to as FRI hereinafter) as *Escherichia coli* IGVT137 (FERM BP-547).

EXAMPLE 2

Construction of recombinant plasmid pGNC5 coding for 1-Ser-137-Cys-IFN-γ(Δ138-146)

In this step, 10 μg of pGVL10 DNA obtained in Reference Example 4 was dissolved in 50 μl of Y-100 buffer solution. 20 units of restriction enzyme HindIII was added and digestion reaction was carried out at 37°

Two single chain DNAs of 18-mer and 17-mer were synthesized by a conventional triester method [R. Crea, et al.: Proc. Natl. Acad. Sci., USA, 75, 5765 (1978)]. Then, 2 μg each of the 18-mer and 17-mer DNAs were dissolved in 40 μl (total volume) of a solution containing 50 mM Tris-HCl (pH 7.5), 10 mM MgCl₂, 5 mM dithiothreitol, 0.1 mM EDTA and 1 mM ATP. 30 units of T4 polynucleotide kinase (product of Takara Shuzo C. for 3 hours. Then, 20 units of restriction enzyme TaqI was added and digestion reaction was carried out at 65° C. for 2 hours. About 0.5 μg of a DNA fragment of about 300 bp containing the 5' terminal region of the IFN-γ structural gene was obtained from the reaction solution by polyacrylamide gel electrophoresis.

Separately, 10 μg of pGVT137 DNA obtained in Example 1 was dissolved in 50 μl of Y-100 buffer solution and 20 units of restriction enzyme BglII was added. Digestion reaction was carried out at 37° C. for 3 hours. Then, 20 units of restriction enzyme TaqI was added and digestion reaction was carried out at 65° C. for 2 hours. About 0.4 μg of a DNA fragment of about 130 bp containing the 3' terminal region of the IFN-γ structural gene was obtained from the reaction solution by polyacrylamide gel electrophoresis.

Separately, 5 μg of plasmid pGVT137 DNA was dissolved in 50 μl of Y-100 buffer solution and 10 units each of restriction enzymes HindIII and BglII were added. Digestion reaction was carried out at 37° C. for 3 hours.

About 2.0 μg of a DNA fragment of about 4.6 Kb containing the 3' non-translational region and Ptrp was obtained from the reaction solution by LFT method.

Then, 0.4 μg of the HindIII-TaqI fragment (about 300 bp) derived from pGVL10, 0.5 μg of the BglII-TaqI fragment (about 130 bp) derived from pGVT137 and 1.0 μg of the HindIII-BglII fragment (about 4.6 Kb) derived from the same plasmid which were obtained above were dissolved in 25 μl of T4 ligase was buffer solution. 6 units of T4 DNA ligase was added and ligation reaction was carried out at 4° C. for 17 hours.

*Escherichia coli* HB101 strain was transformed with the resulting recombinant plasmid mixture to obtain an Ap$^R$ colony.

Figure 2:
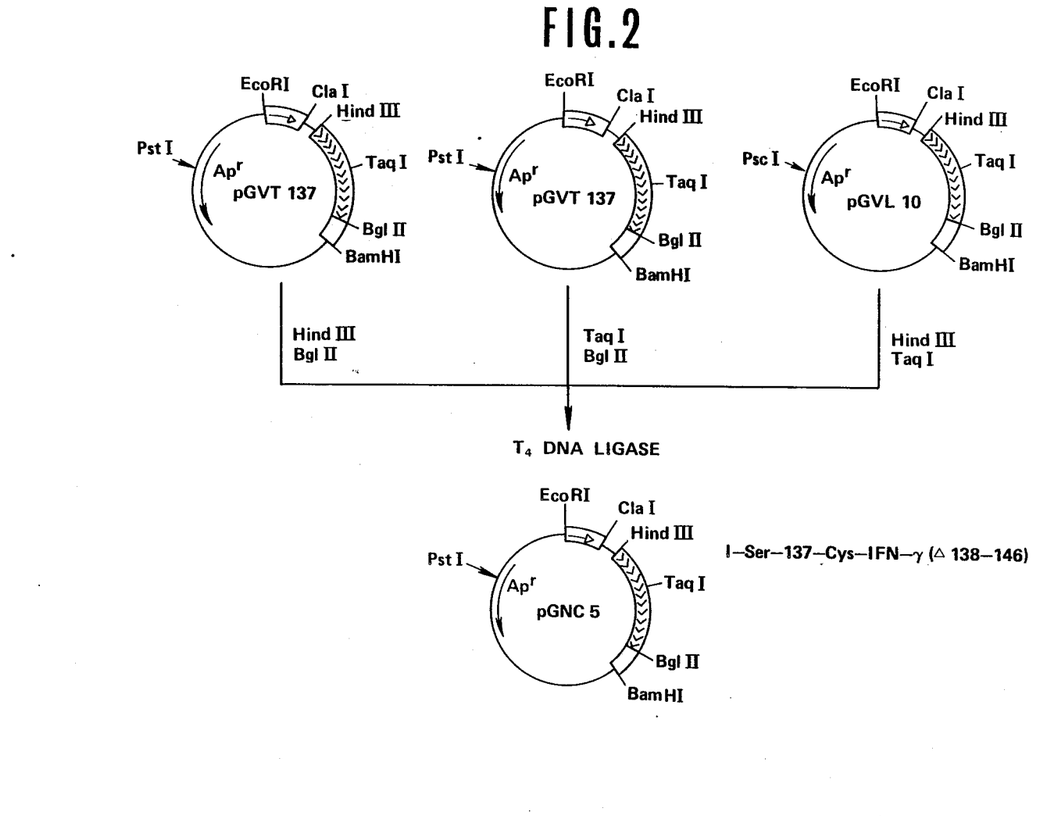
FIG. 2 is a flow sheet for the construction of plasmid pGNC5. As the sites for TaqI, only those which are used for the construction are indicated.

Plasmid pGNC5 illustrated in FIG. 2 was isolated from the culture both of the colony. The structure of pGNC5 was confirmed by the digestion with HindIII, EcoRI, BglII, ClaI and BamHI and agarose gel electrophoresis. It was confirmed by the method of Maxam-Gilbert that the DNA sequence around HindIII-SinI in pGNC5 was as follows:

and the DNA sequence around HinfI-TaqI was as follows:

The human IFN-γ polypeptide derivative encoded by pGNC5 [the derivative is named 1-Ser-137-Cys-IFN-γ(Δ138–146)] is clearly different from the known human IFN-γ polypeptide in that the first amino acid (Cys) of the mature human IFN-γ is replaced with Ser, the 137th amino acid (Met) is replaced with Cys and the 9 amino acids from the C-terminal 138th amino acid (Leu) to 146th amino acid (Gln) are deleted. *Escherichia coli* strain carrying plasmid pGNC5 has been deposited with FRI as *Escherichia coli* IGNC5 (FERM BP-550).

EXAMPLE 3

Construction of recombinant plasmid pGNB4 coding for 3-Ser-137-Cys-IFN-γ (Δ138–146)

In this step, 10 μg of pGVM101 DNA obtained in Reference Example 5 was dissolved in 50 μl of Y-100 buffer solution. 20 units of restriction enzyme HindIII was added and digestion reaction was carried out at 37° C. for 3 hours. Then, 20 units of restriction enzyme TaqI was added and digestion reaction was carried out at 65° C. for 2 hours. About 0.5 μg of a DNA fragment of about 300 bp containing the 5' terminal region of the IFN-γ structural gene was obtained from the reaction solution by polyacrylamide gel electrophoresis.

Separately, 10 μg of pGVT137 DNA obtained in Example 1 was dissolved in 50 μl of Y-100 buffer solution and 20 units of restriction enzyme BglII was added. Digestion reaction was carried out at 37° C. for 3 hours. Then, 20 units of restriction enzyme TaqI was added and digestion reaction was carried out at 65° C. for 2 hours. About 0.4 μg of a DNA fragment of about 130 bp containing the 3' terminal region of the IFN-γ structural gene was obtained from the reaction solution by polyacrylamide gel electrophoresis.

Separately, 5 μg of plasmid pGVT137 DNA was dissolved in 50 μl of Y-100 buffer solution and 10 units each of restriction enzymes HindIII and BglII were added. Digestion reaction was carried out at 37° C. for 3 hours.

About 2.0 μg of a DNA fragment of about 4.6 Kb containing the 3' non-translational region and Ptrp was obtained from the reaction solution by LGT method.

Then, 0.4 μg of the HindIII-TaqI fragment (about 300 bp) derived from pGVM101, 0.5 μg of the BglII-TaqI fragment (about 130 bp) derived from pGVT137 and 1.0 μg of the HindIII-BglII fragment (about 4.6 Kb) derived from the same plasmid which were obtained above were dissolved in 25 μl of T4 ligase buffer solution. 6 units of T4 DNA ligase was added and ligation reaction was carried out at 4° C. for 17 hours.

*Escherichia coli* HB101 strain was transformed with the resulting recombinant plasmid mixture to obtain an Ap$^R$ colony.

Figure 3:
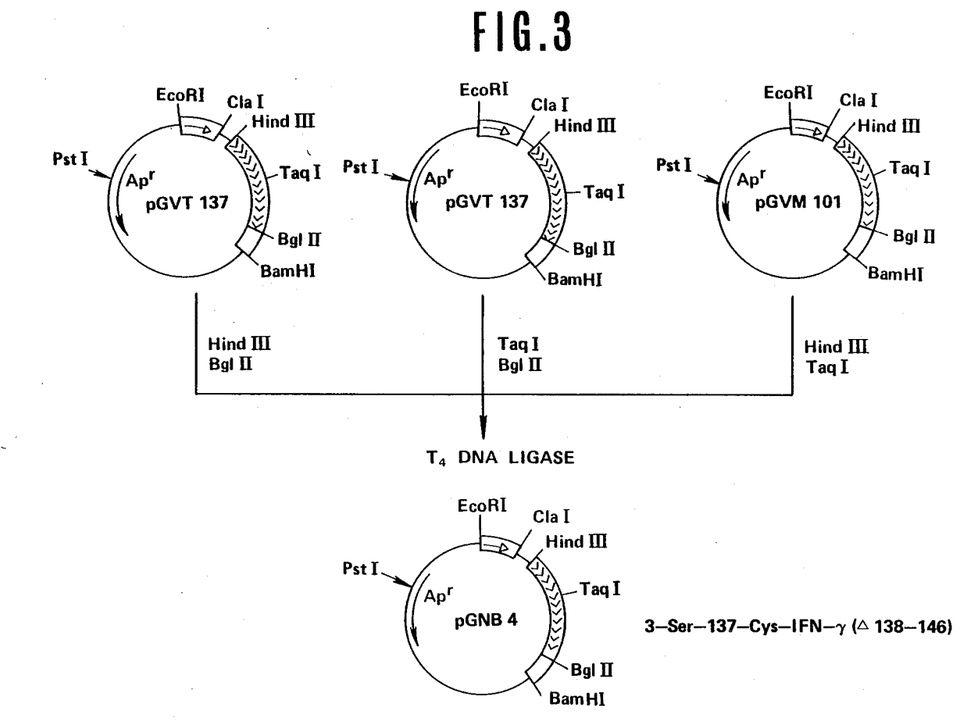
FIG. 3 is a flow sheet for the construction of plasmid pGNB4. As the sites for TaqI, only those which are used for the construction are indicated.

Plasmid pGNB4 illustrated in FIG. 3 was isolated from the culture broth of the colony. The structure of pGNB4 was confirmed by the digestion with HindIII, EcoRI, BglII, ClaI and BamHI and agarose gel electrophoresis. It was confirmed by the method of Maxam-Gilbert that the DNA sequence around HindIII-SinI in pGNB4 was as follows:

and the DNA sequence around HinfI-TaqI was as follows:

The human IFN-γ polypeptide derivative encoded by pGNB4 [the derivative is named 3-Ser-137-Cys-IFN-γ (Δ138–146)] is clearly different from the known human IFN-γ polypeptide in that the third amino acid (Cys) of the mature human IFN-γ is replaced with Ser, the 137th amino acid (Met) is replaced with Cys and the 9 amino acids from the C-terminal 138th amino acid (Leu) to 146th amino acid (Gln) are deleted. *Escherichia coli* strain carrying plasmid pGNB4 has been deposited with FRI as [Escherichia coli IGNB4 (FERM BP-549).

EXAMPLE 4

Construction of recombinant plasmid pGNA3 coding for 1,3-Ser-137-Cys-IFN-γ (Δ138–146)

In this step, 10 μg of pGVK13 DNA obtained in Reference Example 6 was dissolved in 50 μl of Y-100 buffer solution. 20 units of restriction enzyme HindIII was added and digestion reaction was carried out at 37° C. for 3 hours. Then, 20 units of restriction enzyme TaqI was added and digestion reaction was carried out at 65° C. for 2 hours. About 0.05 μg of a DNA fragment of about 300 bp containing the 5' terminal region of the IFN-γ structural gene was obtained from the reaction solution by polyacrylamide gel electrophoresis.

Separately, 10 μg of pGVT137 DNA obtained in Example 1 was dissolved in 50 μl of Y-100 buffer solution and 20 units of restriction enzyme BglII was added. Digestion reaction was carried out at 37° C. for 3 hours. Then, 20 units of restriction enzyme TaqI was added and digestion reaction was carried out at 65° C. for 2 hours. 0.4 μg of a DNA fragment of about 130 bp containing the 3' terminal region of the IFN-γ structural gene was obtained from the reaction solution by polyacrylamide gel electrophoresis.

Separately, 5 μg of plasmid pGVT137 DNA was dissolved in 50 μl of Y-100 buffer solution and 10 units each of restriction enzymes HindIII and BglII were added. Digestion reaction was carried out at 37° C. for 3 hours.

About 2.0 μg of a DNA fragment of about 4.6 Kb containing the 3' non-translational region and Ptrp was obtained from the reaction solution by LGT method.

Then, 0.4 μg of the HindIII-TaqI fragment (about 300 bp) derived from pGVK13, 0.5 μg of the BglII-TaqI fragment (about 130 bp) derived from pGVT137 and 1.0 μg of the HindIII-BglII fragment (about 4.6 Kb) derived from the same plasmid which were obtained above were dissolved in 25 μl of T4 ligase buffer solution. 6 units of T4 DNA ligase was added and ligation reaction was carried out at 4° C. for 17 hours.

*Escherichia coli* HB101 strain was transformed with the resulting recombinant plasmid mixture to obtain an Ap$^R$ colony.

Figure 4:
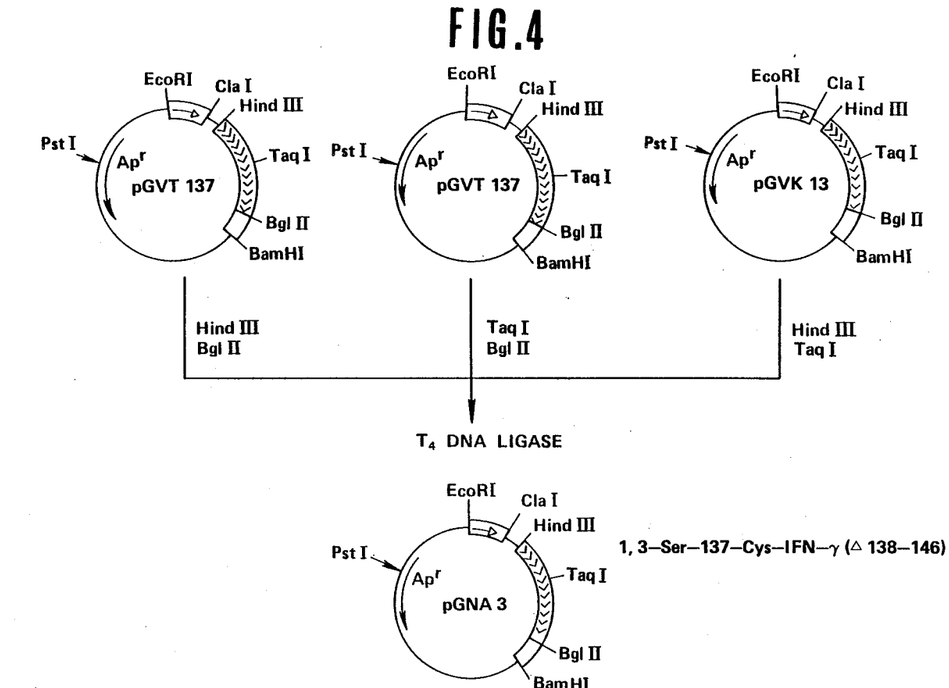
FIG. 4 is a flow sheet for the construction of plasmid pGNA3. As the sites for TaqI, only those which are used for the construction are indicated.

Plasmid pGNA3 illustrated in FIG. 4 was isolated from the culture broth of the colony. The structure of pGNA3 was confirmed by the digestion with HindIII, EcoRI, BglII, ClaI and BamHI and agarose gel electrophoresis. It was confirmed by the method of Maxam-Gilbert that the DNA sequence around HindIII-SinI in pGNA3 was as follows:

and the DNA sequence around HinfI-TaqI was as follows:

The human IFN-γ polypeptide derivative encoded by pGNA3 [the derivative is named 1,3-Ser-137-Cys-IFN-γ (Δ138–146)] is clearly different from the known human IFN-γ polypeptide in that the first and third amino acids (Cys) of the mature human IFN-γ are replaced with Ser, the 137th amino acid (Met) is replaced with Cys and the 9 amino acids from the C-terminal 138th amino acid (Leu) to 146th amino acid (Gln) are deleted. *Escherichia coli* strain carrying plasmid pGNA3 has been deposited with FRI as *Escherichia coli* IGNA3 (FERM BP-548).

EXAMPLE 5

Production of IFN-γ derivatives by *Escherichia Coli* strains carrying pGVT137, pGNC5, pGNB4 and pGNA3

*Escherichia coli* HB101 strains carrying recombinant plasmids pGVT137, pGNC5, pGNB4 and pGNA3 obtained in Examples 1–4, which are named IGVT137, IGNC5, IGNB4 and IGNA3 respectively, were cultured at 37° C. for 18 hours in LG medium (10 g of trypton, 5 g of yeast extract, 5 g of NaCl, 2 g of glucose, 1 l of water, adjusted to pH 7.0 with NaOH). 0.2 ml of the culture broth was inoculated into 10 ml of MCG medium (0.6% Na$_2$HPO$_4$, 0.3% KH$_2$PO$_4$, 0.5% NaCl, 0.1% NH$_4$Cl, 0.5% glucose, 0.5% casamino acid, 1 mM MgSO$_4$, 4 μg/ml vitamine B, pH 7.2) and culturing was carried out at 30° C. for 4-8 hours. Then, 10 μg/ml indolylacrylic acid (referred to as IAA hereinafter) which is an inducer of tryptophan was added and culturing was continued for 2-12 hours. The culture broth was centrifuged at 8,000 rpm for 10 minutes and the cells harvested were washed with a buffer solution containing 30 mM NaCl and 30 mM Tris-HCl (pH 7.5). Washed cells were suspended in 1 ml of the buffer solution described above and 5 μl of a solution containing 200 μg of lysozyme and 0.25M EDTA (ethylenediamine tetraacetic acid) was added. The mixture was allowed to stand at 0° C. for 30 minutes and freezing and thawing were repeated three times to disrupt the cells. The disrupted cells were centrifuged at 15,000 rpm for 30 minutes to obtain a supernatant fluid. The amount of interferon in the supernatant was determined according to the method of Armstrong [J. A. Armstrong, et al.: Appl. Microbiol. 21, 723-725 (1971)], wherein Sindvis virus was used as the virus and FL cells derived from human amnion cells were used as the animal cells. The results are shown in Table 2.

TABLE 2

| Strain | Plasmid | Product encoded by the plasmid | IFN—γ (units/ml) |
|---|---|---|---|
| IGVT137 | pGVT137 | 137-Cys—IFN—γ (Δ138-146) | 8 × 10$^4$ |
| IGNA3 | pGNA3 | 1,3-Ser—137-Cys—IFN—γ (Δ138-146) | 8 × 10$^5$ |
| IGNB4 | pGNB4 | 3-Ser—137-Cys—IFN—γ (Δ138-146) | 1 × 10$^6$ |
| IGNC5 | pGNC5 | 1-Ser—137-Cys—IFN—γ (Δ138-146) | 5 × 10$^5$ |
| IGKA2 | pGKA2 | IFN—γ | 2 × 10$^4$ |

IGKA2 is a strain carrying plasmid pGKA2 coding for IFN-γ.

EXAMPLE 6

Experiment on heat stability of IFN-γ derivatives; 137-Cys-IFN-γ(Δ138-146), 1-Ser-137-Cys-IFN-γ(Δ138-146), 3-Ser-137-Cys-IFN-γ(Δ138-146) and 1,3-Ser-137-Cys-IFN-γ(Δ138-146):

*Escherichia coli* HB101 strains carrying recombinant plasmids pGVT137, pGNC5, pGNB4 and pGNA3 obtained in Examples 1-4, which are named IGVT137, IGNC5, IGNB4 and IGNA3 respectively, were cultured at 37° C. for 18 hours in LG medium. 0.2 ml of the culture broth was inoculated into 10 ml of MCG medium and culturing was carried out at 30° C. for 4-8 hours. Then, 10 μg/ml IAA was added and culturing was continued for 2-12 hours. The culture broth was centrifuged at 8,000 rpm for 10 minutes and the cells harvested were washed with 30 mM Tris-HCl (pH 7.5) buffer solution containing 30 mM NaCl. Washed cells were suspended in 1 ml of the buffer solution described above and 5 μl of a solution containing 200 μg of lysozyme and 0.25M EDTA was added. The mixture was allowed to stand at 0° C. for 30 minutes and freezing and thawing were repeated three times to disrupt the cells. The disrupted cells were centrifuged at 15,000 rpm for 30 minutes to obtain a supernatant fluid.

The supernatant was heated at 50° C. for one hour and the anti-viral activity of interferon was determined according to the method of Armstrong to measure the residual activity (%).

The results are shown in Table 3.

TABLE 3

| Strain | Plasmid | Product encoded by the plasmid | Residual activity after heat treatment at 50° C. for 1 hour (%) |
|---|---|---|---|
| IGVT137 | pGVT137 | 137-Cys—IFN—γ (Δ138-146) | 81 |
| IGNC5 | pGNC5 | 1-Ser—137-Cys—IFN—γ(Δ138-146) | 86 |
| IGNB4 | pGNB4 | 3-Ser—137-Cys—IFN—γ(Δ138-146) | 98 |
| IGNA3 | pGNA3 | 1,3-Ser—137-Cys—IFN—γ(Δ138-146) | 23 |
| IGKA2 | pGKA2 | IFN—γ | 25 |

REFERENCE EXAMPLE 1

Insertion of human IFN-γ DNA into the expression vector pKYP11:

In this example, 6 μg of plasmid pIFNγ-G4 (3.6 Kb) was dissolved in 50 μl (total volume) of a solution containing 20 mM Tris-HCl (pH 7.5), 10 mM MgCl$_2$, 10 mM dithiothreitol and 50 mM NaCl. Then, 12 units each of restriction enzymes PvuII and HindIII were added and digestion reaction was carried out at 37° C. for 4 hours. The reaction solution was heated at 65° C. for 7 minutes to inactivate the enzymes and subjected to purification by LGT method to obtain 1.2 μg of a DNA fragment of 1.3 Kb containing human IFN-γ DNA.

Separately, 4 μg of pKYP11 was dissolved in 40 μl (total volume) of a solution containing 20 mM Tris-HCl (pH 7.5), 10 mM MgCl$_2$, 10 mM dithiothreitol and 50 mM NaCl. 8 units of BamHI was added and digestion reaction was carried out at 37° C. for 3 hours. The reaction solution was heated at 65° C. for 5 minutes to inactivate the enzyme. Thereafter, 30 μM each of dATP, dCTP, dGTP and dTTP were added and 8 units of *Escherichia coli* DNA polymerase I (Klenow fragment, product of New England Biolabs, 1 μl) was added. Fill-in reaction was carried out at 15° C. for one hour and the reaction solution was heated at 68° C. for 15 minutes to inactivate DNA polymerase I. 10 units of HindIII was added and digestion reaction was carried out at 37° C. for 3 hours, followed by heating at 65° C. for 5 minutes to inactivate HindIII. The digestion reaction solution of the plasmid pKYP11 was subjected to purification by LGT method to obtain about 2.5 μg of a DNA fragment of about 4.7 Kb containing P$_{trp}$.

Then, 0.5 μg of the DNA fragment of 1.3 Kb containing human IFN-γ DNA and 1.0 μg of the DNA fragment of about 4.7 Kb containing P$_{trp}$, which was obtained from the plasmid pKYP11, were dissolved in 20 μl of a solution containing 20 mM Tris-HCl (pH 7.5), 6 mM MgCl$_2$, 5 mM dithiothreitol and 500 μM ATP, and 4 units of T4 DNA ligase was added. Ligation reaction was carried out at 4° C. for 18 hours, and *Escherichia coli* HB101 was transformed with the resulting recombinant plasmid mixture by conventional technique to obtain an Ap$^R$ colony. Plasmid pGC7 was separated from the culture broth of the colony. The structure of pGC7 was confirmed by the digestion with HindIII, HpaI, SalI, EcoRI and ClaI and agarose gel electrophoresis. *Escherichia coli* strain containing pGC7 has been deposited with FRI as *Escherichia coli* IGC7 (FERM BP-497).

REFERENCE EXAMPLE 2

Construction of recombinant plasmid pGKA2

In this example, 6 μg of the pGC7 DNA obtained in Reference Example 1 was dissolved in 50 μl (total volume) of a solution containing 20 mM Tris-HCl (pH 7.5), 10 mM MgCl₂, 10 mM dithiothreitol and 10 mM NaCl, and 12 units of BstNI (product of New England Biolabs) was added. Reaction was carried out at 60° C. for 3 hours, and the reaction solution was heated at 65° C. for 5 minutes to inactivate BstNI. Then, NaCl was added to a final concentration of 150 mM and 8 units of SalI was added. Digestion reaction was carried out at 37° C. for 3 hours. The reaction solution was again heated at 65° C. for 5 minutes to inactivate SalI and subjected to purification by LGT method to obtain about 0.8 μg of a DNA fragment of about 1,125 bp containing a large portion of the human IFN-γ DNA.

Separately, 3 μg of pKYP10 was dissolved in 40 μl (total volume) of a solution containing 20 mM Tris-HCl (pH 7.5), 10 mM MgCl₂, 10 mM dithiothreitol and 100 mM NaCl. 6 units each of HindIII and SalI were added and digestion reaction was carried out at 37° C. for 3 hours. The reaction solution was heated at 65° C. for 5 minutes to inactivate HindIII and SalI and subjected to purification by LGT method to obtain about 1.8 μg of a DNA fragment of about 4.1 Kb containing $P_{trp}$.

The N-terminal amino acid of the mature human IFN-γ polypeptide is Cys. In order to express mature IFN-γ DNA, it is necessary to furnish an initiation codon (ATG) just before the 5'-terminal codon TGT (Cys) and further to adjust the length between SD-sequence downstream from $P_{trp}$ and ATG to a suitable length of 6–18 bp. Therefore, the following DNA linker was synthesized.

Two single chain DNAs of 18-mer and 15-mer were synthesized by a conventional triester method. Then, 2 μg each of the 18-mer and 15-mer DNAs were dissolved in 20 μl (total volume) of a solution containing 50 mM Tris-HCl (pH 7.5), 10 mM MgCl₂, 5 mM dithiothreitol, 0.1 mM EDTA and 1 mM ATP. 30 units of T4 polynucleotide kinase (product of Boehringer Mannheim GmbH) was added and phosphorylation reaction was carried out at 37° C. for 60 minutes.

Then, 2 μg each of phosphorylated 18-mer and 15-mer DNAs were mixed and the mixture was heated at 70° C. and 5 minutes and allowed to stand at room temperature for annealing to obtain the DNA linker having the structure given above.

0.4 μg of the BstNI-SalI fragment of 1,125 bp obtained above and derived from pGC7 and 1.0 μg of the DNA fragment of 4.1 Kb obtained by digestion of the expression vector pKYP10 with HindIII and SalI were dissolved in 25 μl (total volume) of a solution containing 20 mM Tris-HCl (pH 7.5), 6 mM MgCl₂, 5 mM dithiothreitol and 500 μM ATP. About 0.1 μg of the DNA linker mentioned above was added to the mixture, followed by addition of 6 units of T4 DNA ligase.

Ligation reaction was carried out at 4° C. for 17 hours. *Escherichia coli* HB101 was transformed using the resulting recombinant plasmid mixture by conventional technique to obtain an $Ap^R$ colony. A plasmid, pGKA2 illustrated in FIG. 1 was isolated from the culture broth of the colony. The structure of pGKA2 was confirmed by the digestion with EcoRI, ClaI, HindIII, BstNI and SalI and agarose gel electrophoresis. It was confirmed by the method of Maxam-Gilbert that the DNA sequence from the SD-sequence (AAGG) to the initiation codon (ATG) in the plasmid pGKA2 was "AAGG-GTATCGATAAGCTTATG".

*Escherichia coli* strain containing pGKA2 has been deposited with FRI as *Escherichia coli* IGKA2 (FERM BP-496).

REFERENCE EXAMPLE 3

Construction of plasmid pGBD1 having BamHI cleavage site downstream from IFN-γ gene In this example, 2 μg of plasmid pIFNγ-G4 (3.6 Kb) was dissolved in 50 μl (total volume) of a solution containing 20 mM Tris-HCl (pH 7.5), 10 mM MgCl₂, 10 mM dithiothreitol and 50 mM NaCl (referred to as "Y-50 buffer solution" hereinafter). Then, 4 units of restriction enzyme PvuII was added and digestion reaction was carried out at 37° C. for 2 hours. The digest was subjected to purification by LGT method to obtain 1 μg of a DNA fragment (3.6 Kb) of pIFNγ-G4. 0.1 μg of the DNA fragment and 5 pmoles of 5'-phosphorylated BamHI linker (5'-pCCGGATCCGG-3': product of Collaborative Research, Inc.) were ligated at 4° C. for 18 hours with 2 units of T4 ligase in 20 μl of T4 ligase in 20 μl of T4 ligase buffer solution.

*Escherichia coli* HB101 [Boliver, et al.: GENE 2, 75 (1977)] was transformed using the thus obtained recombinant plasmid DNA by the method of Cohen, et al. [S. N. Cohen, et al.: Proc. Natl. Acad. Sci. USA. 69, 2110 (1972)] to obtain an $Ap^R$ colony. Plasmid DNA was isolated from the transformant by the known method [H. C. Birnboim, et al.: Nucleic Acids Res., 7, 1513 (1979)]. The DNA was digested with restriction endonucleases such as BamHI and its structure was analyzed to recognize that recombinant plasmid pGBD1 wherein BamHI linker was inserted into PvuII site of pIFNγ-G4 was obtained. *Escherichia coli* strain carrying plasmid pGBD1 has been deposited with FRI as *Escherichia coli* IGBD1 (FERM BP-394).

REFERENCE EXAMPLE 4

Construction of recombinant plasmid pGVL10 coding for 1-Ser-IFN-γ

In this example, 6 μg of pGBD1 DNA obtained in Reference Example 3 was dissolved in 50 μl of Y-50 buffer solution, 10 units of SinI was added and digestion reaction was carried out at 37° C. for 3 hours. Then, NaCl was added to a final concentration of 100 mM and 10 units of BamHI was added. Digestion reaction was carried out at 37° C. for 3 hours. 0.8 μg of a DNA fragment of about 850 bp containing a large portion of the human IFN-γ DNA was obtained from the reaction solution by LGT method.

Separately, 3 μg of pKYP10 DNA prepared by the method described in Japanese Published Unexamined Patent Application No. 110600/83 was dissolved in 40 μl (total volume) of Y-50 buffer solution and 5 units each of HindIII and BamHI were added. Digestion reaction was carried out at 37° C. for 3 hours. From the reaction solution, about 1.8 μg of a DNA fragment of about 4.3 Kb containing tryptophan promoter (P$_{trp}$) was obtained by LGT method.

Mature human IFN-γ polypeptide has the N-terminal structure of Cys-Tyr-Cys-. In order to change the first Cys to Ser and to furnish an initiation codon (ATG) necessary for expression just before the first Set, the following DNA linker was synthesized.

Two single chain DNAs of 20-mer and 19-mer were synthesized by a conventional triester method. Then, 2 μg each of the 20-mer and 19-mer DNAs were dissolved in 40 μl (total volume) of a solution containing 50 mM Tris-HCl (pH 7.5), 10 mM MgCl$_2$, 5 mM dithiothreitol, 0.1 mM EDTA and 1 mM ATP. 30 units of T4 polynucleotide kinase was added and phosphorylation reaction was carried out at 37° C. for 60 minutes.

0.5 μg of the SinI-BamHI fragment of about 850 bp derived from pGBD1 and 1.0 μg of the HindIII-BamHI fragment of about 4.3 Kb of the expression vector pKYP10 which were obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

*Escherichia coli* HB101 was transformed using the resulting recombinant plasmid mixture to obtain an Ap$^R$ colony. A plasmid, pGVL10 illustrated in FIG. 2 was isolated from the culture broth of the colony. The structure of pGVL10 was confirmed by the digestion with EcoRI, ClaI, HindIII and BamHI and agarose gel electrophoresis. It was confirmed by the method of Maxam-Gilbert that the DNA sequence from the HindIII site to the SinI site in the plasmid pGVL10 was as follows.

The human IFN-γ polypeptide encoded by pGVL10 (the derivative is named 1-Ser-IFN-γ) is clearly different from the known human IFN-γ polypeptide in that the first Cys of the mature human IFN-γ is replaced by Ser. *Escherichia coli* strain carrying plasmid pGVL10 has been deposited with FRI as *Escherichia coli* IGVL10 (FERM BP-544).

REFERENCE EXAMPLE 5

Construction of recombinant plasmid pGVM101 coding for 3-Ser-IFN-γ:

In this example, 6 μg of pGBD1 DNA obtained in Reference Example 3 was dissolved in 50 μl of Y-50 buffer solution. 10 units of SinI was added and digestion reaction was carried out at 37° C. for 3 hours. Then, NaCl was added to a final concentration of 100 mM and 10 units of BamHI was added. Digestion reaction was carried out at 37° C. for 3 hours. 0.8 μg of a DNA fragment of about 850 bp containing a large portion of the human IFN-γ DNA was obtained from the reaction solution by LGT method.

Separately, 3 μg of pKYP10 DNA prepared by the method described in Japanase Published Unexamined Patent Application No. 110600/83 was dissolved in 40 μl (total volume) of Y-50 buffer solution and 5 units each of HindIII and BamHI were added. Digestion reaction was carried out at 37° C. for 3 hours. From the reaction solution, about 1.8 μg of a DNA fragment of about 4.3 Kb containing tryptophan promoter (P$_{trp}$) was obtained by LGT method.

Mature human IFN-γ polypeptide has the N-terminal structure of Cys-Tyr-Cys-. In order to change the third amino acid (Cys) to Ser and to furnish an initiation codon (ATG) necessary for expression just before the first Cys, the following DNA linker was synthesized.

Two single chain DNAs of 20-mer and 19-mer were synthesized by a conventional triester method. Then, 2 μg each of the 20-mer and 19-mer DNAs were dissolved in 40 μl (total volume) of a solution containing 50 mM Tris-HCl (pH 7.5), 10 mM MgCl$_2$, 5 mM diethiothreitol, 0.1 mM EDTA and 1 mM ATP. 30 units of T4 polynucleotide kinase was added and phosphorylation reaction was carried out at 37° C. for 60 minutes.

0.5 μg of the SinI-BamHI fragment of about 850 bp derived from pGBD1 and 1.0 μg of the HindIII-BamHI fragment of about 4.3 Kb of the expression vector pKYP10 which were obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

*Escherichia coli* HB101 was transformed using the resulting recombinant plasmid mixture to obtain an Ap$^R$ colony. A plasmid, pGVM101, illustrated in FIG. 3 was isolated from the culture broth of the colony. The structure of pGVM101 was confirmed by the digestion with EcoRI, ClaI, HindIII and BamHI and agarose gel electrophoresis. It was confirmed by the method of Maxam-Gilbert that the DNA sequence from the HindIII site to the SinI site in the plasmid pGVM 101 was as follows.

The human IFN-γ polypeptide encoded by pGVM101 (the derivative is named 3-Ser-IFN-γ) is clearly different from the known human IFN-γ polypeptide in that the third amino acid (Cys) of the mature human IFN-γ is replaced with Ser. *Escherichia coli* strain carrying plasmid pGVM101 has been deposited with FRI as *Escherichia coli* IGVM101 (FERM BP-545).

REFERENCE EXAMPLE 6

Construction of recombinant plasmid pGVK13 coding for 1,3-Ser-IFN-γ:

In this example, 6 μg of pGBD1 DNA obtained in Reference Example 3 was dissolved in 50 μl of Y-50 buffer solution. 10 units of SinI (product of Bio Tec Co.) was added and digestion reaction was carried out at 37° C. for 3 hours. Then, NaCl was added to a final concentration of 100 mM and 10 units of BamHI was added. Digestion reaction was carried out at 37° C. for 3 hours. About 0.8 μg of a DNA fragment of about 850 bp containing a large portion of the human IFN-γ DNA was obtained from the reaction solution by LGT method. Separately, 3 μg of pKYP10 was dissolved in 40 μl (total volume) of a solution containing Y-100 buffer solution and 5 units each of HindIII and BamHI were added. Digestion reaction was carried out at 37° C. for 3 hours. From the reaction solution, about 1.8 μg of a DNA fragment of about 4.3 Kb containing $P_{trp}$ was obtained by LGT method.

Mature human IFN-γ polypeptide has the N-terminal structure of Cys-Tyr-Cys-. In order to change the first and third amino acids (Cys) to Ser and to furnish an initiation codon (ATG) necessary for expression just before the first Ser, the following DNA linker was synthesized.

Two single chain DNAs of 20-mer and 19-mer were synthesized by a conventional triester method. Then, 2 μg each of the 20-mer and 19 mer DNAs were dissolved in 40 μl (total volume) of a solution containing 50 mM Tris-HCl (pH 7.5), 10 mM MgCl$_2$, 5 mM dithiothreitol, 0.1 mM EDTA and 1 mM ATP. 30 units of T4 polynucleotide kinase was added and phosphorylation reaction was carried out at 37° C. for 60 minutes.

Then, 0.4 μg of the SinI-BamHI fragment of about 850 bp derived from pGBD1 and 1.0 μg of the HindIII-BamHI fragment of about 4.3 Kb of the expression vector pKYP10 which were obtained above were dissolved in 25 μl of T4 ligase buffer solution. About 0.1 μg of the DNA linker mentioned above was added to the mixture, followed by addition of 6 units of T4 DNA ligase. Ligation reaction was carried out at 4° C. for 17 hours.

*Escherichia coli* HB101 was transformed using the resulting recombinant plasmid mixture to obtain an Ap$^R$ colony. A plasmid, pGVK13 illustrated in FIG. 4 was isolated from the culture broth of the colony. The structure of pGVK13 was confirmed by the digestion with EcoRI, HindIII, ClaI and BamHI and agarose gel electrophoresis. It was confirmed by the method of Maxam-Gilbert that the DNA sequence from the HindIII site to the SinI site in the plasmid pGVK13 was as follows.

The human IFN-γ polypeptide encoded by pGVK13 (the derivative is named 1,3-Ser-IFN-γ) is clearly different from the known human IFN-γ polypeptide in that the first and third amino acids (Cys) of the mature human IFN-γ are replaced with Ser. *Escherichia coli* strain carrying plasmid pGVK13 has been deposited with FRI as *Escherichia coli* IGVK13 (FERM BP-432).

What is claimed is:

1. A derivative of human interferon-γ polypeptide comprising an amino acid sequence in which nine amino acid residues have been removed from the carboxy terminus thereof, the methionine residue at position 137 has been replaced with a cysteine and the amino acid at positions 1 and 3 may be serine or cysteine and which is encoded by a recombinant plasmid selected from the group consisting of pGVT137, pGNC5 and pGNB4.

* * * * *

UNITED STATES PATENT AND TRADEMARK OFFICE
CERTIFICATE OF CORRECTION

PATENT NO. : 4,898,931
DATED : February 6, 1990
INVENTOR(S) : SEIGA ITOH ET AL.

It is certified that error appears in the above-identified patent and that said Letters Patent is hereby corrected as shown below:

COLUMN 6

Line 26, "endonucleasees" should read --endonucleases--.
    Line 62, "polypeptide" should read --polypeptides--.

COLUMN 9

Line 1, "restriction enzyme BgIII" should read --restriction enzyme BglII--.
    Line 16, "LFT method." should read --LET method.--.

COLUMN 11

Line 41, "0.05 µg" should read --0.5 µg--.

COLUMN 13

Line 4, "vitamine B," should read --vitamine $B_1$,--.

COLUMN 15

Line 57, "and" should read --for--.

COLUMN 17

Line 65, "by" should read --with--.

UNITED STATES PATENT AND TRADEMARK OFFICE
CERTIFICATE OF CORRECTION

PATENT NO. : 4,898,931

DATED : February 6, 1990

INVENTOR(S) : SEIGA ITOH ET AL.

It is certified that error appears in the above-identified patent and that said Letters Patent is hereby corrected as shown below:

COLUMN 18

Line 40, "diethi-" should read --dithi---.

Signed and Sealed this

Eleventh Day of August, 1992

Attest:

DOUGLAS B. COMER

*Attesting Officer*  *Acting Commissioner of Patents and Trademarks*